(12) United States Patent
Yamaguchi et al.

(10) Patent No.: US 6,340,539 B1
(45) Date of Patent: *Jan. 22, 2002

(54) 2,5-DIMERCAPTO-1,3,4-THIADIAZOLE DILITHIUM SALT AND ITS DIHYDRATE AND THEIR MANUFACTURE, AND A SECONDARY LITHIUM BATTERY AND POSITIVE ELECTRODE-ACTIVE MATERIAL COMPRISING THE SAME

(75) Inventors: Satoshi Yamaguchi; Satoshi Nakagawa; Sunao Mitsui; Susumu Ohno, all of Takasago (JP)

(73) Assignee: Toyo Kasei Kogyo Company Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/337,469

(22) Filed: Jun. 21, 1999

(30) Foreign Application Priority Data

Jun. 23, 1998 (JP) .............................. 10-193729
Jun. 23, 1998 (JP) .............................. 10-193730
Jun. 23, 1998 (JP) .............................. 10-193731

(51) Int. Cl.$^7$ ..................... H01M 4/60; C07D 285/125; C07D 285/12
(52) U.S. Cl. ....................... 429/213; 548/142
(58) Field of Search ................. 429/321, 188, 429/213; 548/142

(56) References Cited

FOREIGN PATENT DOCUMENTS

| EP | 0 497 308 A2 | | |
|---|---|---|---|
| EP | 0 497 308 A3 | 8/1992 | 8/1992 |
| JP | 04-267073 | 9/1992 | |
| JP | 04-267074 | 9/1992 | |
| JP | 05-314964 | 11/1993 | |

OTHER PUBLICATIONS

Pope et al. "Organosulfur/conducting polymer composite cathodes. Voltammetric study of the polymerization and depolymerization of 2,5,–dimercapto–1,3,4–thiadiazole in acetonitrile" J. Electrochem. Soc. Jun. 1998 145 (6), 1893–1901, Jun. 1998.*

Pope et al. "Spectroscopic identification of 2,5,–dimercapto–1,3. 4–thiadiazole and its lithium salt and dimer forms" J. Power Sources (1997) 69(2), 739–742.*

Picart et al. "Electrochemical study of 2, 5–dimercapto–1, 3,4–thiadiazole in acetonitrile" J. Electroanal. Chem. 1996, 408(1–2), 53–60.*

* cited by examiner

Primary Examiner—Laura Weiner
(74) Attorney, Agent, or Firm—Wenderoth, Lind & Ponack, L.L.P.

(57) ABSTRACT

This invention is directed to 2,5-dimercapto-1,3,4-thiadiazole dilithium salt and its dihydrate and methods of their manufacture, and a secondary lithium battery and positive electrode-active material comprising the same.

22 Claims, 1 Drawing Sheet

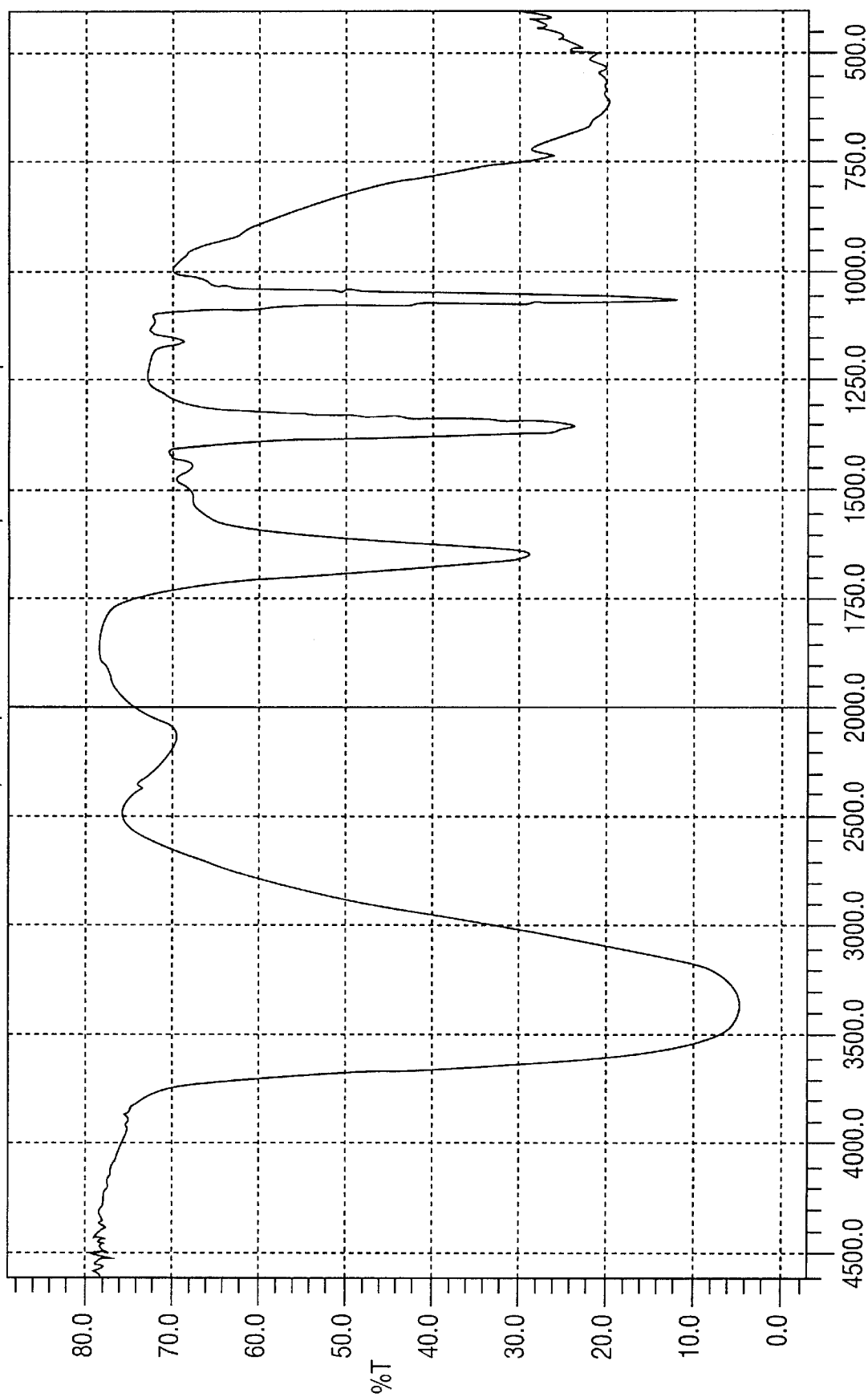
FIG. 1  The infrared absorption spectrum of the compound of Example 1.

2,5-DIMERCAPTO-1,3,4-THIADIAZOLE DILITHIUM SALT AND ITS DIHYDRATE AND THEIR MANUFACTURE, AND A SECONDARY LITHIUM BATTERY AND POSITIVE ELECTRODE-ACTIVE MATERIAL COMPRISING THE SAME

BACKGROUND OF THE INVENTION

1. Field of the Invention

This invention relates to methods for manufacturing a dilithium salt of 2,5-dimercapto-1,3,4-thiadiazole (DMcT) (hereinafter referred to as $Li_2DMcT$) and $Li_2DMcT$ dihydrate. The $Li_2DMcT$ dihydrate manufactured by this invention is an industrially very useful substance which is used widely, for example, as a photosensitive material for photos, a dye, an inhibitor, a surface-treating agent for metals, a raw material for additives to lubricating oils, a monomer for high refractive index plastics, an electrode material for lithium batteries, and a starting material or intermediate for medicines and agricultural chemicals.

2. Description of the Related Art

DMcT dilithium salt (abbreviated to $Li_2DMcT$ hereafter) is very hygroscopic and deliquescent, and its isolation is very difficult; therefore nothing has been reported on its properties, and its handling has been hard. In addition, neither has the existence of its dihydrate been clearly reported nor it has been even suggested. Besides it is known that thiol compounds are easy to oxidize and that addition of alkali to them further facilitates their oxidation. This is true also of $Li_2DMcT$; $Li_2DMcT$ is easily oxidized by air. This has raised a problem in trying isolation of $Li_2DMcT$; the crystallization doesn't go well when the compound's purity is low, and yet the application of a purification process to the compound makes its purity lower because of the oxidation.

The need for size and weight reduction of portable equipment and the consideration on the environment and energy issues have promoted very much the research and development of high energy density secondary batteries for years.

Particularly secondary lithium batteries have been developed remarkably. While at present the positive electrode material is mainly a metal oxide such as lithium cobaltate, etc., research on the use of organic compounds as a positive electrode material has been attracting attention on the grounds that such an electrode may achieve higher energy density than that of today's batteries using metal oxides. Of the organic compounds thiols are the most promising, and attempts to make use of the reversibility of thiols' oxidation and reduction reaction for the second battery have been made. One of those attempts was made by Koyama et al., who reported on the use of DMcT as a positive electrode material (Nature, vol.373, No.6515, p.598–600,1995); the battery in this report achieved high energy density by using as positive electrode a composite electrode made of conductive polyaniline and the thiol compound. In another example, i.e., in tokukaihei (Japanese Patent Application Publication No. 4-26704), Ueno et al. reported the use of lithium thiolate as a positive electrode material, and metallic aluminum or its alloy together with a carbon material as a negative electrode. Besides the current-voltage characteristic is lowered when an aluminum alloy containing 30 atom % lithium is used as a negative electrode; from this result, there will be a problem of battery performance degradation if metallic lithium is used as a negative electrode.

The inventors of the present invention developed various polythiol compounds and studied batteries using those compounds as a positive electrode material, but could not obtain a favorable battery because of the following problems:

1) bad cycle characteristics
2) odor of the compound used
3) generation of hydrogen gas during the initial charging and discharging
4) low heat stability of the compound used
5) in the case of a liquid polythiol compound, vaporization of the polythiol in the positive electrode-drying process The use of the lithium salts of those polythiols as a positive electrode-active material and metallic lithium as a negative electrode-active material resulted in further lowering the cycle characteristics and also posed a problem of hydrogen gas generation during the initial charging and discharging.

SUMMARY OF THE INVENTION

The objective of this invention is to solve the problems listed above and provide methods for manufacturing $Li_2DMcT$ and $Li_2DMcT$ dihydrate, the compounds of which having as mentioned above a wide range of uses as a photosensitive material for photos, a dye, an inhibitor, a surface-treating agent for metals, a raw material for additives to lubricating oils, a monomer for high refractive index plastics, an electrode material for lithium batteries, and a starting material or intermediate for medicines and agricultural chemicals.

BRIEF DESCRIPTION OF THE DRAWINGS

FIG. 1 shows the chart of the infrared absorption spectrum of the compound of Example 1 in this invention.

DESCRIPTION OF THE PREFERRED EMBODIMENTS

For accomplishment of these objects, the present invention provides a method for manufacturing $Li_2DMcT$ dihydrate as represented in the formula (1), which method comprises adjusting a molar ratio of lithium in a lithiation agent to 2 to 3 relative to DMcT in a solvent, and allowing the DMcT to react with the lithiation agent at 0 to 120° C.

(1)

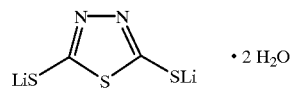

The present invention also provides a method for manufacturing $Li_2DMcT$ as represented by the formula (2), which method comprises heating $Li_2DMcT$ dihydrate represented by the formula (1) at 200° C. or higher to dryness.

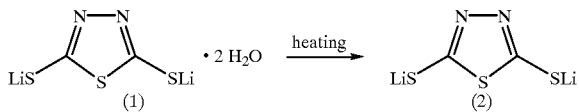

The present invention further provides another method for manufacturing $Li_2DMcT$ as represented by the formula (2), which method comprises adding DMcT with a lithiation agent selected from the group consisting of metallic lithium, lithium hydride and lithium ethoxide, and allowing the DMcT to react with the lithiation agent in a non-aqueous system.

It has been found that Li$_2$DMcT dihydrate of this invention is of high quality when in the reaction of DMcT with a lithiation agent the mole ratio of lithium in the lithiation agent to DMcT is adjusted to 2. It has been also found in this invention that Li$_2$DMcT dehydrate is less hygroscopic and less diliquescent than anhydrous Li$_2$DMcT so the dehydrate has an advantage over the anhydrous salt in isolability and handleability. In the method of this invention for manufacturing Li$_2$DMcT dihydrate, the reaction of DMcT with a lithiation agent is carried out with the mole ratio of lithium in the lithiation agent to DMcT of 2. When the mole ratio is greater than 2, Li$_2$DMcT dehydrate is obtained but its purity is lowered because of the remaining lithiation agent. When the mole ratio is less than 2, the thiol groups remains, resulting in greater formability of the disulfide by-products by the reason mentioned above and less stability of the product compound. Thus the mole ratio of lithium in the lithiation agent to DMcT should be 1.8–3.0 or more preferably 1.9–2.5.

Any lithiation agent can be used so far as it is one commonly used for that purpose; lithium hydroxide, lithium carbonate, etc. are preferable because they are very available and less expensive; particularly lithium hydroxide is more preferable because its high purity article is on the market. As for a solvent for the reaction, one which can dissolve Li$_2$DMcT is preferable; the following can be used; water and alcohols such as methanol, ethanol, etc., polar aprotic solvents like dimethlformamide (DMF), and solvents such as tetrahydrofuran (THF), dioxane, etc. The following solvents can also be used in this synthesis if alcohol or water and alcohol are added: ethers such as diethyl ether, etc., aromatic compounds such as benzene toluene, etc., aliphatic compounds such as n-hexane, etc., and ketones such as acetone, methyl ethyl ketone, etc. The reaction temperature should be 0–120° C. because of decomposition of DMcT at higher temperatures, and the more preferable temperature is 10–100° C. The appropriate reaction time is 1 minute–10 hours, or more preferably 5 minutes–1 hours. Besides DMcT is known to decompose at its melting point, i.e., at about 172° C.; however, the decomposition temperature is much lowered when impurities are contained. The inventors' study has confirmed that the decomposition temperature is about 30° C. lowered to 140° C. when several percent of impurities from oxidation of DMcT are contained. Therefore DMcT is not a favorable compound if reactions or treatments at high temperatures are required.

The inventors have confirmed that, by changing the polythiol compound into its lithium salt and then by isolating the salt and drying to make it anhydrous, the hydrogen generation can be avoided completely and the odor emission in the process of the positive electrode fabrication, which was a problem in the case of polythiol compounds, also can be avoided completely. In addition, the use of a polythiol's lithium salt instead of the polythiol itself has solved the problem of thiol vaporization in the process of drying the positive electrode because replacing a liquid polythiol with its salt which is solid makes the pertinent boiling point much higher; a polythiol's lithium salt has broadened the applicable range of polythiols.

Further the inventors have found that the isolation of lithium thiolates and elimination of water from them by drying improve the cycle characteristics so much that even the use of metallic lithium as a negative electrode can give a good result. Take DMcT for example. DMcT is known to decompose at its melting point, i.e., at about 170° C. but the decomposition temperature decreases when impurities are contained; according to the inventors' study, the decomposition temperature is lowered to about 140° C. when the impurities from oxidation of DMcT are contained by several percent; thus DMcT cannot be said to be advantageous as a material for batteries. In contrast, DMcT dilithium salt represented by the formula (2) above has proved to have heat-stability improved remarkably, having a decomposition temperature of about 340° C. Li$_2$DMcT is usually produced in the form of dihydrate, but it has been found that Li$_2$DMcT can be made anhydrous by drying at 200° C.

In the past the use of metallic lithium as a negative electrode material posed problems such as hydrogen gas generation during the initial charging and discharging, and the cycle characteristics lowering, but the inventors have solved these problems by once isolating Li$_2$DMcT dihydrate and then drying it enough to make it anhydrous. As described hitherto, the inventors' study has found positive electrode-active materials for batteries which can improve cycle characteristics, prevent hydrogen gas generation and provide safety, and achieve high energy density; thus this invention has been completed.

The thermal analysis of Li$_2$DMcT dihydrate, the new compound discovered in this invention, has shown that it has a decomposition temperature of about 341° C. and has a much higher heat-stability than DMcT. As this invention shows, Li$_2$DMcT dihydrate of such a high quality is obtained when the mole ratio of lithium to DMcT in the reaction to produce the dilithium salt is adjusted to 2. Li$_2$DMcT dihydrate is more soluble in polar solvents such as water, alcohol, etc. than DMcT, so it can improve the volume efficiency. It also brings another remarkable advantage: its high heat-stability enables it to be applied to areas for which DMcT cannot be used.

EXAMPLES

The invention is illustrated in the following examples but is not limited only to the examples.

Example 1

0.63 g (14.90 mmol) of lithium hydroxide monohydrate (content 99.95%) and 5.9 g of distilled water were charged to a reaction vessel and the lithium hydroxide monohydrate was dissolved. 150 ml of ethanol was added to this solution. The mixture was made homogeneous by agitation and then the atmosphere was replaced with nitrogen. 275 ml of ethanol and 275 ml of diethyl ether were placed in another vessel, whose atmosphere was then replaced with nitrogen. To this vessel 1.12 g (7.45 mmol) of DMcT (content 99%) was charged and replacement with nitrogen was conducted again. After that, the alcoholic solution of lithium hydroxide already prepared was added dropwise to the DMcT solution, while the temperature of the droplets of the lithium hydroxide solution was kept at 20° C. or lower. After completion of the dropwise addition, the mixture was stirred for 30 minutes at a reaction temperature of 20° C., and then the mixture was subjected to concentration under reduced pressure to distill out ethanol and diethyl ether. To the remaining solution, 300 ml of toluene was added and concentration under reduced pressure was applied again. After repeating this procedure three times, 10 ml of toluene was added to the remaining solution; then the crystal matter was separated by filtration and was dried under vacuum at 60° C. for 24 hours. Thus 1.47 g of DMcT dilithium salt dihydrate, a white crystal, was obtained (yield 99%). The results of NMR, elementary analysis and thermal analysis are shown below, and the chart of infrared absorption spectrum is given in FIG. 1. The result of the elementary analysis confirmed the formation of Li$_2$DMcT dihydrate.

NMR $^1$H, NMR δ ppm, 4.74(s. H$_2$O), $^{13}$C, NMR δ ppm, 177.48(s. C).

Elementary analysis

|                    | C     | H    | N     | S     |
|--------------------|-------|------|-------|-------|
| Observed values    | 12.01 | 2.27 | 14.09 | 48.51 |
| Calculated values  | 12.12 | 2.04 | 14.14 | 48.55 |

Thermal analysis

| Weight loss beginning point | 183.1° C.: (weight loss at 18.2%) |
|  | 329.6° C. |
| Endothermic peak | 194.2° C. |
| Exothermic peak | 341.6° C. |

Example 2

1.00 g of DMcT dilithium salt dihydrate obtained by the method of Example 1 was dried for 24 hours at 200° C. under reduced pressure. Thus 0.81 g of DMcT dilithium salt, a white crystal, was obtained (yield 99%). The results of NMR spectroscopy analysis and elementary analysis are shown below:

NMR spectroscopy analysis $^1$H, NMR δ ppm, peak is not detected, $^{13}$C, NMR δ ppm, 177.82(s.C).

Elementary analysis

|                    | C     | H    | N     | S     |
|--------------------|-------|------|-------|-------|
| Observed values    | 14.71 | 0.03 | 17.21 | 59.16 |
| Calculated values  | 14.81 | 0.00 | 17.28 | 59.34 |

Example 3

0.1 g (14.90 mmol) of Metallic Li (purity 99.9%) and 100 ml of ethanol charged to a reaction vessel and then the atmosphere was replaced with nitrogen. 275 ml of ethanol and 275 ml of diethylether were placed in another vessel, whose atmosphere was then replaced with nitrogen. Previous prepared alcoholic solution of metallic Li is poured with that vessel under the temperature of 20° C.

After the above pouring of that alcoholic solution into the vessel is finished, said alcoholic solution is agitated for 30 minutes, at 20° C. and ethanol and diethylether are removed by distillation under reduced pressure and then 10 ml toluene is added to the remained alcoholic solution.

And after the solution is agitated, obtained crystals are filtered and dried at 60° C. for 18 hours under reduced pressure. Thus 1.2 g of DMcT dilithium salt, a white crystal, was obtained (yield 99%).

Example 4

1.5 weight parts of anhydrous DMcT dilithium salt was dissolved in 7.0 weight parts of NMP and a homogeneous viscous solution was obtained. To this solution 1.0 weight part of polyaniline was added and dissolved to produce a homogeneous solution. To this solution 5 weight parts of acetylene black was added and dispersed uniformly by agitation. This solution was applied to a piece of 30-μm-thick Cu foil with 1 μm Ag plating, and the foil piece was dried under vacuum at 80° C. for one hour. Thus a positive electrode of a 20 mm×20 mm sheet was obtained. As a negative electrode, a 300-μm-thick, 20 mm×20 mm lithium foil piece was used. Lithium borofluride was added to a 1:1 mixed solution of propylene carbonate and ethylene carbonate; to the resultant solution a copolymer of acrylonitrile and vinyl acetate was added, and the mixture was stirred to make a homogeneous solution; then by cooling the solution to 20° C. a polymer gel electrolyte was obtained. The composite positive electrode, negative electrode, and electrolyte thus obtained, were put in a sealed alminum laminate container; this formed a battery.

DMcT dilithium salt and its dehydrate of invention are more soluble in polar solvents and much more heat-stable than DMcT, so they can be used not only in the application areas in which DMcT has been used but also in areas for which DMcT has not been suitable. This is a remarkable advantage of theirs.

Furthermore, the dilithium salt of this invention are positive electrodeactive materials for batteries which will provide good cycle characteristics and good safety, and also are compounds which will enable the development of what is sought today, i.e., a secondary battery having high energy density. Further, it has been confirmed that the use of the anhydrous lithium thiolate of invention enables the manufacture of good batteries even when metallic lithium is used as a negative electrode material. Besides the use of the anhydrous lithium thiolate of this invention enables the manufacture of secondary batteries having no positive electrode film expansion, which expansion has been a problem in the use of thiol compounds; thus the thiolate is a material which can be used in commercial battery production.

What is claimed is:

1. A method for manufacturing dilithium salt dihydrate of 2,5-dimercapto-1,3,4-thiadiazole represented by the formula (1), which method comprises adding 2,5-dimercapto-1,3,4-thiadiazole with a lithiation agent, adjusting a molar ratio of lithium in a lithiation agent to 1.8 to 3 relative to 2,5-dimercapto-1,3,4-thiadiazole in a solvent, and allowing the 2,5-dimercapto-1,3,4-thiadiazole to react with the lithiation agent at 0 to 120° C. to obtain the dilithium salt dihydrate of 2,5-dimercapto-1,3,4-thiadiazole represented by the formula (1).

(1)

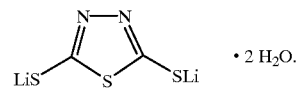

· 2 H$_2$O.

2. A method for manufacturing a dilithium salt of 2,5-dimercapto-1,3,4-thiadiazole represented by the formula (2), which method comprises obtaining a dilithium salt dihydrate of 2,5-dimercapto-1,3,4-thiadiazole represented by the formula (1) according to the method of claim 1, and heating said dilithium salt dihydrate of 2,5-dimercapto-1,3,4-thiadiazole represented by the formula (1) at 200° C. or higher to dryness to obtain the dilithium salt of 2,5-dimercapto-1,3,4-thiadiazole represented by the formula (2).

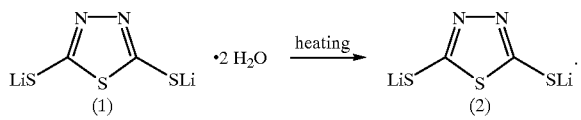

3. The method for manufacturing the dilithium salt of 2,5-dimercapto-1,3,4-thiadiazole according to claim 2, wherein the lithiation agent is selected from the group consisting of metallic lithium, lithium hydride, and lithium ethoxide.

4. The method for manufacturing the dilithium salt of 2,5-dimercapto-1,3,4-thiadiazole according to claim 3 wherein the 2,5-dimercapto-1,3,4-thiadiazole is reacted with the lithiation agent in a non-aqueous system.

5. A secondary lithium battery comprising (a) a dilithium salt of 2,5-dimercapto-3,4-thiadiazole represented by the formula (2), said dilithium salt being used as a positive electrode-active material and being obtained by the method according to claim 3, and (b) a metallic lithium being used as a negative electrode-active material.

6. A positive electrode-active material comprising a dilithium salt of 2,5-dimercapto-1,3,4-thiadiazole represented by the formula (2), said dilithium salt being obtained by the method according to claim 3.

7. The method for manufacturing the dilithium salt of 2,5-dimercapto-1,3,4-thiadiazole according to claim 2, wherein the 2,5-dimercapto-1,3,4-thiadiazole is reacted with the lithiation agent in a non-aqueous system.

8. A secondary lithium battery comprising (a) a dilithium salt of 2,5-dimercapto-1,3,4-thiadiazole represented by the formula (2), said dilithium salt being used as a positive electrode-active material and being obtained by the method according to claim 7, and (b) a metallic lithium being used as a negative electrode-active material.

9. A positive electrode-active material comprising a dilithium salt of 2,5-dimercapto-1,3,4-thiadiazole represented by the formula (2), said dilithium salt being obtained by the method according to claim 7.

10. The method for manufacturing the dilithium salt of 2,5-dimercapto-1,3,4-thiadiazole according to claim 2, wherein the molar ratio of lithium in a lithiation agent is adjusted to 2 to 3 relative to 2,5-dimercapto-1,3,4-thiadiazole in a solvent.

11. A secondary lithium battery comprising (a) a dilithium salt of 2,5-dimereapto-1,3,4-thiadiazole represented by the formula (2), said dilithium salt being used as a positive electrode-active material and being obtained by the method according to claim 10, and (b) a metallic lithium being used as a negative electrode-active material.

12. A positive electrode-active material comprising a dilithium salt of 2,5-dimercapto-1,3,4-thiadiazole represented by the formula (2), said dilithium salt being obtained by the method according to claim 10.

13. The method for manufacturing the dilithium salt of 2,5-dimercapto-1,3,4-thiadiazole according to claim 2, wherein the molar ratio of lithium in a lithiation agent is adjusted to about 2 relative to 2,5-dimercapto-1,3,4-thiadiazole in a solvent.

14. A secondary lithium battery comprising (a) a dilithium salt of 2,5-dimercapto-1,3,4-thiadiazole represented by the formula (2), said dilithium salt being used as a positive electrode-active material and being obtained by the method according to claim 13, and (b) a metallic lithium being used as a negative electrode-active material.

15. A positive electrode-active material comprising a dilithium salt of 2,5-dimercapto-1,3,4-thiadiazole represented by the formula (2), said dilithium salt being obtained by the method according to claim 13.

16. A secondary lithium battery comprising (a) a dilithium salt of 2,5-dimercapto-1,3,4-thiadiazole represented by the formula (2), said dilithium salt being used as a positive electrode-active material and being obtained by the method according to claim 2, and (b) a metallic lithium being used as a negative electrode-active material.

17. A positive electrode-active material comprising a dilithium salt of 2,5-dimercapto-1,3,4-thiadiazole represented by the formula (2), said dilithium salt being obtained by the method according to claim 2.

18. The method for manufacturing the dilithium salt dihydrate of 2,5-dimercapto-1,3,4thiadiazole according to claim 1, wherein the lithiation agent is selected from the group consisting of metallic lithium, lithium hydride, and lithium ethoxide.

19. The method for manufacturing the dilithium salt dihydrate of 2,5-dimercapto-1,3,4-thiadiazole according to claim 18, wherein the 2,5-dimercapto-1,3,4-thiadiazole is reacted with the lithiation agent in a non-aqueous system.

20. The method for manufacturing the dilithium salt dihydrate of 2,5-dimercapto-1,3,4-thiadiazole according to claim 1, wherein the 2,5-dimercapto-1,3,4-thiadiazole is reacted with the lithiation agent in a nonaqueous system.

21. The method for manufacturing the dilithium salt dihydrate of 2,5-dimercapto-1,3,4-thiadiazole according to claim 1, wherein the molar ratio of lithium in a lithiation agent is adjusted to 2 to 3 relative to 2,5-dimercapto-1,3,4-thiadiazole in a solvent.

22. The method for manufacturing the dilithium salt dihydrate of 2,5-dimercapto-1,3,4-thiadiazole according to claim 1, wherein the molar ratio of lithium in a lithiation agent is adjusted to about 2 relative to 2,5-dimercapto-1,3,4-thiadiazole in a solvent.

* * * * *